(12) United States Patent
Sheldon et al.

(10) Patent No.: US 7,848,808 B2
(45) Date of Patent: Dec. 7, 2010

(54) SYSTEM AND METHOD FOR DELIVERY OF CARDIAC PACING IN A MEDICAL DEVICE IN RESPONSE TO ISCHEMIA

(75) Inventors: Todd J. Sheldon, North Oaks, MN (US); William J. Combs, Minnetonka, MN (US); Lee Stylos, Stillwater, MN (US); Steven N. Lu, Fridley, MN (US); Robert J. Nehls, Lakeville, MN (US)

(73) Assignee: Medtronic, Inc., Minneapolis, MN (US)

( * ) Notice: Subject to any disclaimer, the term of this patent is extended or adjusted under 35 U.S.C. 154(b) by 602 days.

(21) Appl. No.: 11/364,828

(22) Filed: Feb. 28, 2006

(65) Prior Publication Data

US 2007/0203524 A1    Aug. 30, 2007

(51) Int. Cl.
*A61N 1/365* (2006.01)
(52) U.S. Cl. .............................. 607/9; 607/17
(58) Field of Classification Search .......... 600/9, 600/14, 28, 509, 515; 607/521, 509, 510, 607/4, 9, 14, 17
See application file for complete search history.

(56) References Cited

U.S. PATENT DOCUMENTS

| | | | |
|---|---|---|---|
| 5,117,824 A | 6/1992 | Keimel et al. | |
| 5,199,428 A | 4/1993 | Obel et al. | |
| 5,354,316 A | 10/1994 | Keimel | |
| 5,441,523 A * | 8/1995 | Nappholz | 607/14 |
| 5,545,186 A | 8/1996 | Olson et al. | |
| 5,749,900 A * | 5/1998 | Schroeppel et al. | 607/4 |
| 6,021,350 A | 2/2000 | Mathson | |
| 6,058,328 A * | 5/2000 | Levine et al. | 607/14 |
| 6,115,628 A | 9/2000 | Stadler et al. | |
| 6,128,526 A * | 10/2000 | Stadler et al. | 600/517 |
| 6,233,486 B1 | 5/2001 | Eckwall et al. | |
| 6,256,538 B1 * | 7/2001 | Ekwall | 607/17 |
| 6,264,606 B1 | 7/2001 | Eckwall et al. | |
| 6,366,812 B1 | 4/2002 | Levine et al. | |
| 6,381,493 B1 * | 4/2002 | Stadler et al. | 607/9 |
| 6,393,316 B1 | 5/2002 | Gillberg et al. | |
| 6,442,429 B1 * | 8/2002 | Hill et al. | 607/14 |
| 6,604,000 B2 | 8/2003 | Lu | |
| 6,772,005 B2 | 8/2004 | Casavant et al. | |
| 6,865,420 B1 | 3/2005 | Kroll | |
| 6,931,281 B2 * | 8/2005 | Bradley et al. | 607/9 |
| 6,937,899 B2 | 8/2005 | Sheldon et al. | |
| 7,076,298 B2 * | 7/2006 | Padmanabhan et al. | 607/14 |
| 7,181,268 B2 * | 2/2007 | Sheldon et al. | 600/513 |
| 7,181,269 B1 * | 2/2007 | Kroll | 600/517 |
| 7,215,997 B2 * | 5/2007 | Yu et al. | 607/18 |
| 7,225,015 B1 * | 5/2007 | Min et al. | 600/517 |
| 7,274,959 B1 * | 9/2007 | Wang et al. | 600/509 |
| 7,277,745 B2 * | 10/2007 | Natarajan et al. | 600/509 |
| 7,283,872 B2 * | 10/2007 | Boute et al. | 607/8 |
| 7,308,306 B1 * | 12/2007 | Park et al. | 607/9 |
| 2003/0045908 A1 * | 3/2003 | Condie et al. | 607/9 |
| 2004/0133247 A1 | 7/2004 | Stahmann et al. | |
| 2005/0075673 A1 | 4/2005 | Warkentin et al. | |

(Continued)

*Primary Examiner*—Michael Kahelin
(74) *Attorney, Agent, or Firm*—Michael C. Soldner

(57) ABSTRACT

An implantable medical device system and method in which the implantable device is adapted to operate in a minimum ventricular pacing mode. The device delivers cardiac pacing pulses in a first pacing mode during a normal mode of operation and upon detecting myocardial ischemia alters the first pacing mode in response to the myocardial ischemia detection.

32 Claims, 6 Drawing Sheets

U.S. PATENT DOCUMENTS

| | | |
|---|---|---|
| 2005/0137631 A1 | 6/2005 | Yu et al. |
| 2005/0245979 A1* | 11/2005 | Belk .......................... 607/14 |
| 2005/0267539 A1 | 12/2005 | Betzold et al. |
| 2006/0161207 A1* | 7/2006 | Busacker et al. ............... 607/9 |
| 2007/0150015 A1* | 6/2007 | Zhang et al. .................. 607/17 |

* cited by examiner

SYSTEM AND METHOD FOR DELIVERY OF CARDIAC PACING IN A MEDICAL DEVICE IN RESPONSE TO ISCHEMIA

TECHNICAL FIELD

The invention relates generally to medical devices, and, in particular, to medical devices capable of controlling delivery of cardiac pacing in response to ischemia.

BACKGROUND

Recently, cardiac pacing protocols employed by implantable cardiac pacemakers and implantable cardioverter defibrillators (ICDs) are aimed at promoting intrinsic conduction and intrinsic depolarization of the ventricles as often as possible while reducing or minimizing ventricular pacing. Such a pacing protocol generally includes pacing in an atrial mode, such as AAI, ADI, AAIR or ADIR mode, while monitoring intrinsic AV conduction. As long as AV conduction is intact, the atrial pacing mode is maintained. If AV conduction is absent, ventricular pacing is delivered, for example in a dual chamber pacing mode such as DDI or DDIR, to ensure ventricular depolarization during AV block.

Many patients implanted with cardiac pacemakers or ICDs have underlying coronary artery disease and are susceptible to myocardial ischemia. When the pacing mode is programmed in a rate responsive mode (e.g. ADIR, DDDR, or DDIR), a higher pacing rate is provided in response to a sensed increase in metabolic need. The higher pacing rate increases the metabolic demand placed on the myocardium, which could lead to ischemia. Patients subjected to minimum ventricular pacing may have long AV conduction times that result in inefficient AV coupling. Inefficient AV coupling can adversely affect cardiac output and subsequently reduce myocardial perfusion leading to myocardial ischemia. Other causes of myocardial ischemia may be disease related. It is desirable to provide cardiac pacing in a manner that does not worsen an ischemic state and may act to alleviate myocardial ischemia.

BRIEF DESCRIPTION OF THE DRAWINGS

Aspects and features of the present invention will be appreciated as the same becomes better understood by reference to the following detailed description of the embodiments of the invention when considered in connection with the accompanying drawings, wherein.

DETAILED DESCRIPTION

In the following description, references are made to illustrative embodiments for carrying out the invention. It is understood that other embodiments may be utilized without departing from the scope of the invention.

Figure 1:
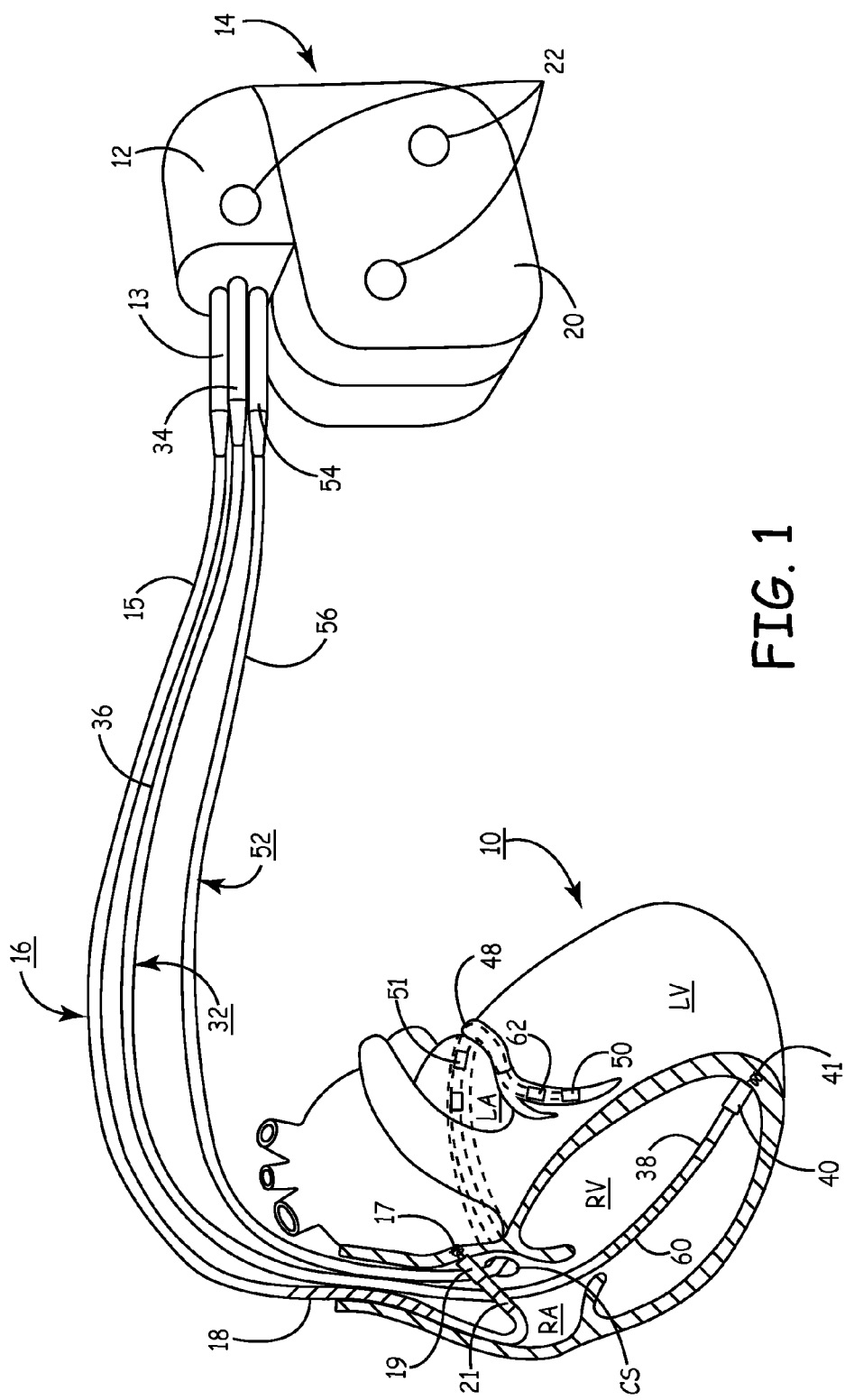
FIG. 1 depicts an implantable, cardiac stimulation device embodied as an ICD 14, in which one embodiment of the present invention may be implemented.

FIG. 1 depicts an implantable, cardiac stimulation device embodied as an ICD 14, in which one embodiment of the present invention may be implemented. ICD 14 is provided for sensing intrinsic heart activity and delivering cardiac stimulation pulses as appropriate to one or more heart chambers. ICD 14 is adapted for delivering minimum ventricular pacing according to a programmed mode of operation.

ICD 14 is shown in communication with a patient's heart 10 by way of three leads 16, 32 and 52. The heart 10 is shown in a partially cut-away view illustrating the upper heart chambers, the right atrium (RA) and left atrium (LA), and the lower heart chambers, the right ventricle (RV) and left ventricle (LV), and the coronary sinus (CS) in the right atrium leading into the great cardiac vein 48, which branches to form inferior cardiac veins. Leads 16, 32 and 52 connect ICD 14 with the RA, the RV and the LV, respectively. Each lead has at least one electrical conductor and pace/sense electrode. A remote indifferent can electrode is formed as part of the outer surface of the ICD housing 20. The pace/sense electrodes and the remote indifferent can electrode can be selectively employed to provide a number of unipolar and bipolar pace/sense electrode combinations for pacing and sensing functions.

RA lead 16 is passed through a vein into the RA chamber and may be attached at its distal end to the RA wall using a fixation member 17. RA lead 16 is formed with a connector 13 fitting into a connector bore of ICD connector block 12 for electrically coupling RA tip electrode 19 and RA ring electrode 21 to ICD internal circuitry via insulated conductors extending within lead body 15. RA tip electrode 18 and RA ring electrode 21 may be used in a bipolar fashion, or in a unipolar fashion with ICD housing 20, for achieving RA stimulation and sensing of RA electrogram (EGM) signals. RA lead 16 is also provided with a coil electrode 18 that may be used for delivering high voltage cardioversion/defibrillation pulses to heart 10 in response to the detection of tachycardia or fibrillation.

RV lead 32 is passed through the RA into the RV where its distal end, carrying RV tip electrode 40 and RV ring electrode 38 provided for stimulation in the RV and sensing of RV EGM signals, is fixed in place in the RV apex by a distal fixation member 41. RV lead 32 also carries a high-voltage coil electrode 60 for use in cardioverting and defibrillating heart 10. RV lead 32 is formed with a connector 34 fitting into a corresponding connector bore of ICD connector block 12. Connector 34 is coupled to electrically insulated conductors within lead body 36 and connected with distal tip electrode 40, ring electrode 38 and coil electrode 60.

Coronary sinus lead 52 is passed through the RA, into the CS and further into a cardiac vein 48 to extend the distal LV tip electrode 50 and ring electrode 62 alongside the LV chamber to achieve LV stimulation and sensing of LV EGM signals. The LV CS lead 52 is coupled at the proximal end connector 54 into a bore of ICD connector block 12 to provide electrical coupling of conductors extending from electrodes 50 and 62 within lead body 56 to ICD internal circuitry. In some embodiments, LV CS lead 52 could bear a proximal LA pace/sense electrode 51 positioned along CS lead body 56 such that it is disposed proximate the LA for use in stimulating the LA and/or sensing LA EGM signals.

In addition to the lead-mounted electrodes, ICD 14 may include one or more cardiac sensing electrodes 22 formed as uninsulated portions of the ICD housing 20 or included in the connector block 12. While a particular ICD system with associated leads and electrodes is illustrated in FIG. 1, numerous implantable cardiac pacemaker and ICD system configurations are possible including one or more leads, which may be transvenous, subcutaneous, or epicardial leads, having various electrode arrangements. Embodiments of the invention may also include subcutaneous pacemaker or ICD systems in which stimulation and sensing electrodes are formed as a part of the device housing and/or carried by subcutaneous leads.

ICD 14 is shown as a multi-chamber device capable of sensing and stimulation in three or all four heart chambers. It is understood that ICD 14 may be modified to operate as a single chamber device for delivering atrial-only pacing (with dual chamber sensing) or a dual chamber device for sensing and stimulation in one upper chamber and one lower chamber. In a single chamber device, ischemia monitoring and monitoring for AV conduction may be performed using subcutaneous electrodes. Furthermore, it is recognized that embodiments of the present invention may be practiced in a single chamber, dual chamber or multi-chamber implantable cardiac pacemaker that does not include cardioversion and defibrillation functions.

Figure 2:
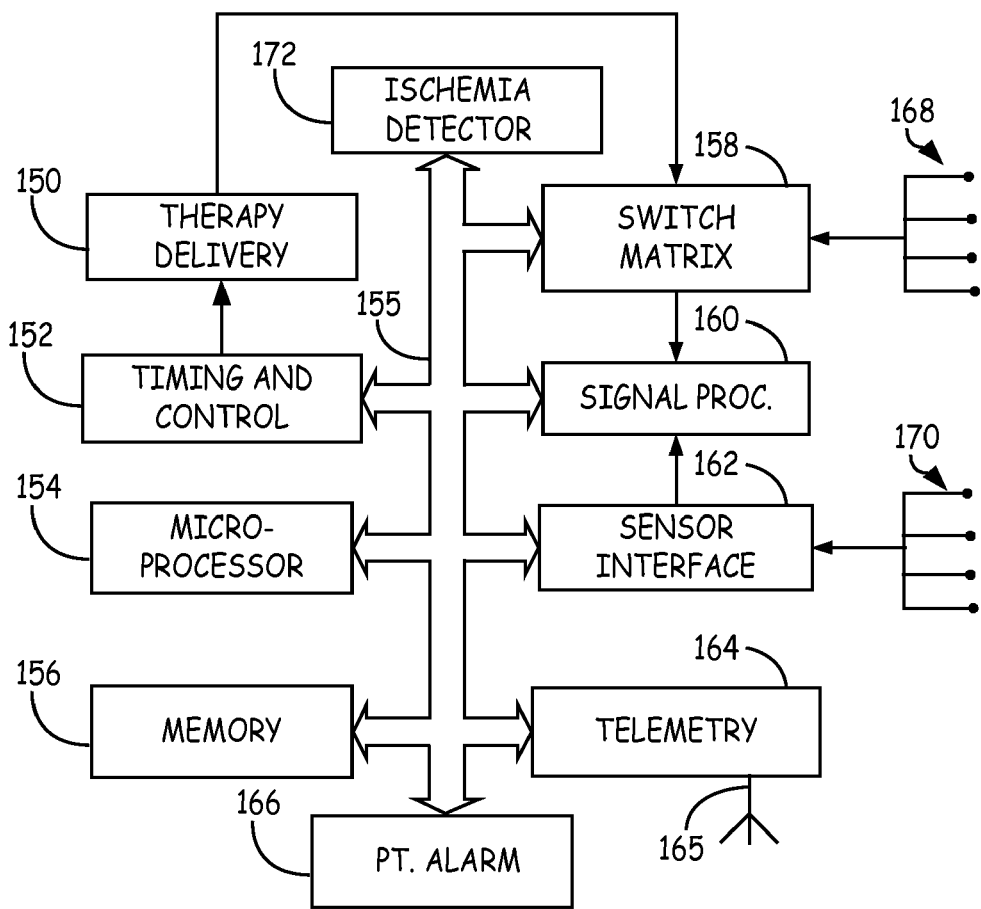
FIG. 2 is a functional block diagram showing some of the components typically included in an implantable cardiac stimulation device such as the ICD shown in FIG. 1.

FIG. 2 is a functional block diagram showing some of the components typically included in an implantable cardiac stimulation device such as the ICD shown in FIG. 1. ICD 14 generally includes timing and control circuitry 152 and an operating system that may employ microprocessor 154 or a digital state machine for timing sensing and therapy delivery functions in accordance with a programmed operating mode. Microprocessor 154 and associated memory 156 are coupled to the various components of IMD 10 via a data/address bus 155. ICD 14 includes therapy delivery unit 150 for delivering electrical stimulation therapies, such as cardiac pacing therapies and arrhythmia therapies including cardioversion/defibrillation shocks, under the control of timing and control 152. Therapy delivery unit 150 is typically coupled to two or more electrode terminals 168 via a switch matrix 158. Switch matrix 158 is used for selecting which electrodes and corresponding polarities are used for delivering electrical stimulation pulses.

Electrode terminals 168 may also be used for receiving electrical signals from the heart or for measuring impedance. Cardiac electrical signals are sensed for determining when an electrical stimulation therapy is needed and in controlling a stimulation mode and the timing of stimulation pulses. Electrodes used for sensing and electrodes used for stimulation may be selected via switch matrix 158. When used for sensing, electrode terminals 168 are coupled to signal processing circuitry 160 via switch matrix 158. Signal processor 160 includes sense amplifiers and may include other signal conditioning circuitry and an analog to digital converter. Electrical signals may then be used by microprocessor 154 for detecting physiological events, such as detecting and discriminating cardiac arrhythmias. Signal processing circuitry 160 may include event detection circuitry generally corresponding to R-wave detection circuitry as disclosed in U.S. Pat. No. 5,117,824 (Keimel, et al.), hereby incorporated herein by reference in its entirety.

Arrhythmia detection algorithms may be implemented for detecting ventricular tachycardia (VT), ventricular fibrillation (VF) as well as atrial arrhythmias such as atrial fibrillation (A FIB). Ventricular event intervals (R-R intervals) sensed from the EGM signals are commonly used for detecting ventricular arrhythmias. Additional information obtained such as R-wave morphology, slew rate, other event intervals (P-R intervals) or other sensor signal information may be used in detecting, confirming or discriminating an arrhythmia. Reference is made to U.S. Pat. No. 5,354,316 (Keimel), U.S. Pat. No. 5,545,186 (Olson et al.) and U.S. Pat. No. 6,393,316 (Gillberg et al.) for examples of arrhythmia detection and discrimination using EGM signals, both of which patents are incorporated herein by reference in their entirety.

In one detection scheme, programmable detection interval ranges designate the range of sensed event intervals indicative of a tachycardia and may be defined separately for detecting slow tachycardia, fast tachycardia and fibrillation. Sensed event intervals falling into defined detection interval ranges are counted to provide a count of tachycardia intervals. A programmable number of intervals to detect (NID) defines the number of tachycardia intervals occurring consecutively or out of a given number of preceding event intervals that are required to detect tachycardia. A separately programmed NID may be defined for detecting slow and fast tachycardia and fibrillation. In addition to the interval ranges and NID criteria, rapid onset criterion and rate stability criterion may also be defined for use in tachycardia detection schemes. Furthermore, a combined count of tachycardia and fibrillation intervals may be compared to a combined count threshold and, according to predefined criteria, used in detecting fibrillation or slow or fast tachycardia.

In addition to event interval information, the morphology of the EGM signal may be used in discriminating heart rhythms, for example as described in the above-incorporated '316 Gillberg patent. According to one embodiment of the invention, digitized EGM signals are provided to microprocessor 154 for waveform analysis according to an implemented morphology or template matching algorithm. Morphology analysis may be used in conjunction with event interval analysis to improve the sensitivity and specificity of arrhythmia detection methods. Since the morphology of the EGM signals is generally altered during ischemia, the waveform analysis used for detecting arrhythmias may be adjusted in response to detecting an ischemic episode according to one embodiment of the invention. For example, the morphology templates and/or correlation coefficients used in EGM waveform analysis for detecting arrhythmias may be different during an ischemic episode than during a non-ischemic episode.

In response to an arrhythmia detection, a programmed arrhythmia therapy is delivered by therapy deliver module 150 under the control of timing and control 152. A description of high-voltage output circuitry and control of high-voltage shock pulse delivery is provided in the above-incorporated '186 Olson patent. Typically, a tiered menu of arrhythmia therapies are programmed into the device ahead of time by the physician and stored in memory 156. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher level cardioversion pulse may be selected thereafter. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is above a preset threshold.

In the event that fibrillation is identified, high frequency burst stimulation may be employed as the initial attempted therapy. Subsequent therapies may be delivery of high amplitude defibrillation pulses, typically in excess of 5 joules. Lower energy levels may be employed for cardioversion. The defibrillation pulse energy may be incremented in response to failure of an initial pulse or pulses to terminate fibrillation.

The occurrence of arrhythmias may be associated with a variety of pathological conditions. The ischemic myocardium is generally more vulnerable to arrhythmias and may be less responsive to arrhythmia therapies than non-ischemic myocardium. Accordingly, as will be described in greater detail below, one embodiment of the invention includes altering programmed arrhythmia therapies in response to a detected ischemic episode.

Cardiac electrical signals may also used in detecting an ischemic episode. For example, electrical signals may be used for detecting changes in an EGM/ECG signals, such as changes in the S-T segment, indicative of myocardial ischemia. Methods for detecting ischemia using ST segment changes are generally described in U.S. Pat. No. 6,128,526 (Stadler, et al.) and U.S. Pat. No. 5,199,428 (Obel et al.), both of which patents are incorporated herein by reference in their entireties. Electrical signals received at terminals 168 may be provided to dedicated ischemia detector circuitry 172 for detecting changes in the signals indicative of an ischemic state. Alternatively, microprocessor 154 may execute ischemia detection algorithms using sensed cardiac electrical signals for detecting an ischemic episode.

ICD 14 may additionally or alternatively be coupled to one or more physiological sensors via physiological sensor terminals 170. Physiological sensors may include pressure sensors, accelerometers, flow sensors, blood chemistry sensors, activity sensors or other physiological sensors known for use with implantable cardiac stimulation devices. Physiological sensors may be carried by leads extending from ICD 14 or incorporated in or on the ICD housing.

Signals received at sensor terminals 170 are received by a sensor interface 162 which provides sensor signals to signal processing circuitry 160. Sensor signals are used by microprocessor 154 for detecting physiological events or conditions. For example, ICD 14 may monitor heart wall motion, blood pressure, blood chemistry, respiration, or patient activity. Monitored signals may be used for sensing the need for delivering a therapy under control of the operating system. In some embodiments, microprocessor 154 or ischemia detector 172 use physiological signals received from sensor terminals 170 for use in detecting myocardial ischemia. For example, an accelerometer signal, a pressure sensor signal, an impedance signal, or an oxygen saturation, pH or other blood chemistry sensor signal may be used alone or in combination with cardiac electrical signals for detecting myocardial ischemia.

The operating system includes associated memory 156 for storing a variety of programmed-in operating mode and parameter values that are used by microprocessor 154. The memory 156 may also be used for storing data compiled from sensed physiological signals and/or relating to device operating history for telemetry out on receipt of a retrieval or interrogation instruction. All of these functions and operations are known in the art, and many are generally employed to store operating commands and data for controlling device operation and for later retrieval to diagnose device function or patient condition. An ischemia detection algorithm may be stored in memory 156 and executed by microprocessor 154 with input received from electrode terminals 168 and/or sensor terminals 170 for detecting ischemia. Alternatively, ischemia detector 172 may be embodied as dedicated circuitry for receiving cardiac EGM/ECG or other physiological signals and for generating a signal indicating detection of myocardial ischemia. As will be described below, timing and control 152 responds to the detection of ischemia by altering a pacing mode, pacing parameter, arrhythmia detection parameter, and/or arrhythmia therapy according to ischemia response data stored in memory 156. Data relating to ischemia detection may be stored in memory 156 for later retrieval.

ICD 14 further includes telemetry circuitry 164 and antenna 128. Programming commands or data are transmitted during uplink or downlink telemetry between ICD telemetry circuitry 164 and external telemetry circuitry included in a programmer or monitoring unit. Telemetry circuitry 164 and antenna 128 may correspond to telemetry systems known in the art. In one embodiment, telemetry circuitry 164 is adapted to receive signals from an external patient activator, home monitor or other external device operable by a patient or caregiver. The patient or caregiver, using the external device, may manually generate a telemetry signal indicating the patient is experiencing symptoms relating to myocardial ischemia. Upon receipt of the external signal, microprocessor 154 causes timing and control 152 to provide an ischemia response.

ICD 14 may optionally be equipped with patient alarm circuitry 166 for generating audible tones, a perceptible vibration, muscle stimulation or other sensory stimulation for notifying the patient that a patient alert condition has been detected by ICD 14. In some embodiments, an alarm signal may be generated upon detection of ischemia or upon altering a pacing mode of operation in response to ischemia detection.

Figure 3:
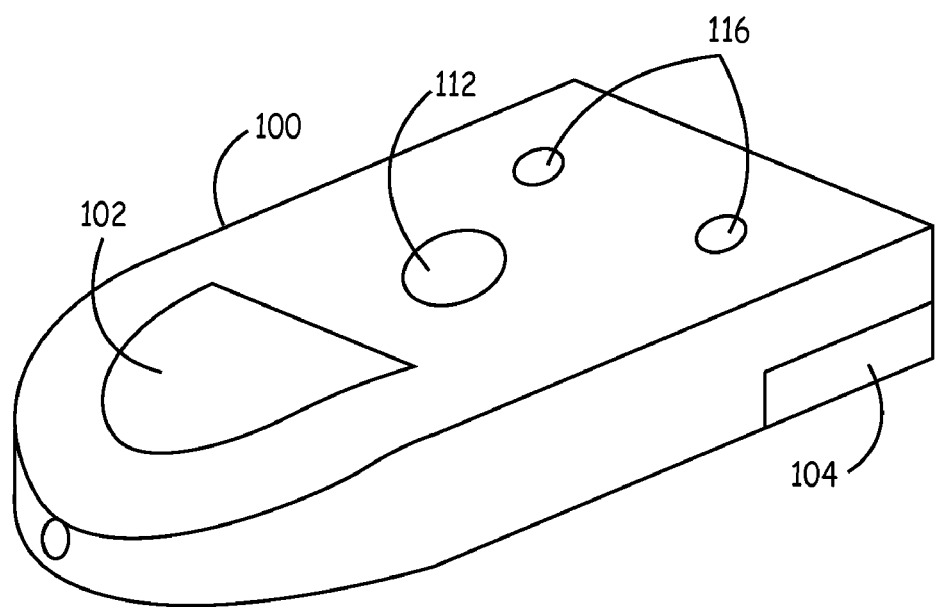
FIG. 3 illustrates the general physical configuration of one external device that may be used to manually indicate an ischemic episode.

FIG. 3 illustrates the general physical configuration of one external device that may be used to manually indicate an ischemic episode. The external device shown in FIG. 3 is embodied as a handheld device known as a patient activator 100. Activator 100 generally takes the form of a plastic enclosure provided with a push button 102 by which the patient or a caregiver may generate an ischemia signal upon presenting symptoms associated with myocardial ischemia, such as angina. The ischemia signal is transmitted to an implanted device, such as ICD 14 shown in FIG. 2, adapted to receive such a signal and provide an ischemia response thereto. Activator 100 is battery powered, employing batteries accessible by means of the battery cover 104. LED indicator lights 116 and a speaker 112 may be provided to communicate to the patient the status and functioning of telemetry communication with the implanted device and the status of a patient-initiated ischemia response. It is to be understood that other types of external devices enabled for telemetric communication with ICD 14 may be used for manually generating an ischemia signal. Such devices include programmers and home monitors.

Figure 4:
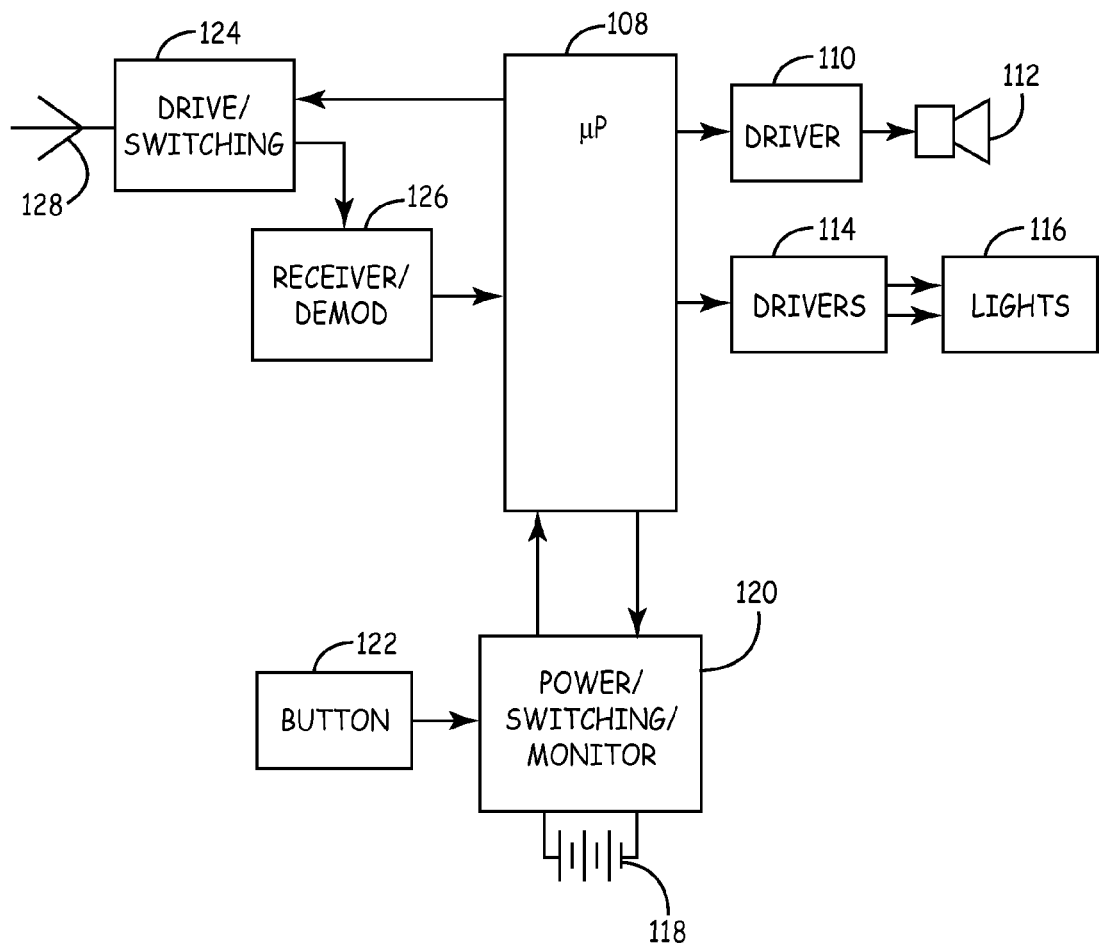
FIG. 4 is a block functional diagram of the patient activator shown in FIG. 3.

FIG. 4 is a block functional diagram of a patient activator. Control functions are provided by microprocessor 108, based upon programming stored in its associated read-only memory located therein. Microprocessor 108 provides output signals for producing audible patient alert signals by means of driver 110 and speaker 112. Microprocessor 108 also provides control signals to LED driver 114 to power associated colored LED indicator lights 116, referred to above. The device is powered by a battery 118 which is coupled to the microprocessor 108 by means of power/switching/battery monitor circuitry 120, which also provides the microprocessor with an indication that push button 122 has been pressed.

Communication with microprocessor 108 is accomplished by means of the antenna driver/switching circuit 124, the receiver demodulator 126 and RF antenna 128. Transmissions from the implanted device are received by antenna 128, and are demodulated by receiver demodulator 126 to be provided to the microprocessor. In response to received transmissions from the implanted device, the microprocessor controls operation of the audio and light drivers 110 and 114 to indicate the nature of the communication received. Transmissions to the implanted device, for example, in response to activation of the push button 102 are provided by microprocessor 108 to the antenna drive/switching circuit, which then communicates with the implanted device by means of antenna 128.

Figure 5:
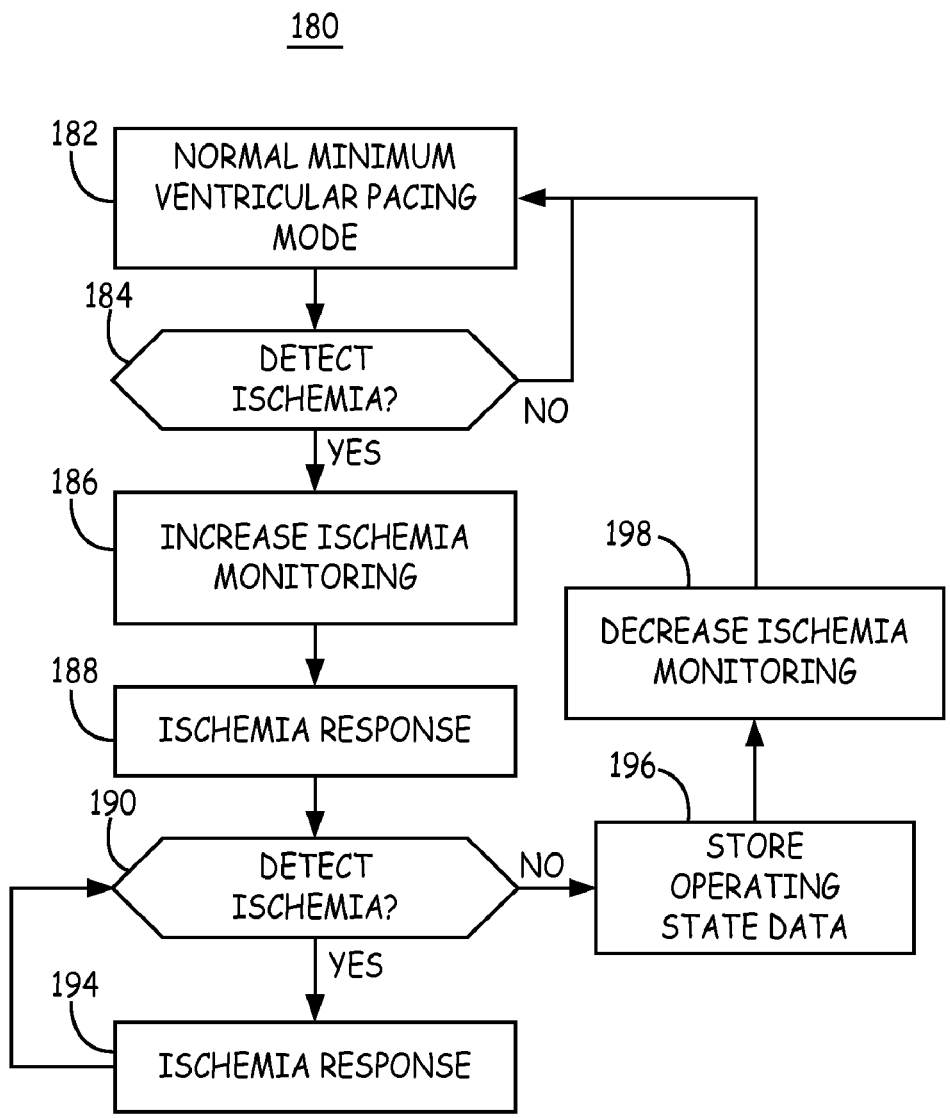
FIG. 5 is a flow chart providing an overview of a method for monitoring for myocardial ischemia and providing an ischemia response.

FIG. 5 is a flow chart providing an overview of a method for monitoring for myocardial ischemia and providing an ischemia response. Flow chart 180 is intended to illustrate functional operations of a pacemaker or ICD, generally referred to hereafter as a "device". Flow chart 180 should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the present invention in the context of any modern ICD, given the disclosure herein, is within the abilities of one of skill in the art.

At block 182, the device operates in a normal minimum ventricular pacing mode, which includes delivery of cardiac pacing pulses as needed and may include monitoring for arrhythmias and delivering programmed arrhythmia therapies. It should be appreciated that the description herein is provided as an overview to illustrate various embodiments for practicing the invention and is not intended to be limiting. For example, reference to a minimum ventricular pacing mode may refer to an operational state that includes mode switches from one pacing mode to another. Alternatively, a minimum ventricular pacing mode may refer to a single operational mode that effectuates both atrial based and dual chamber based functionality aimed at allowing intrinsic AV conduction whenever possible. Thus, for purposes of description, references to a pacing mode and to pacing control parameters with regard to minimum ventricular pacing and an ischemia response are indicative of the functionality imparted and may include an actual mode status switch or a change in the functional status of a single mode inclusive of the altered functions provided in response to ischemia.

Furthermore, it is recognized that the normal minimum ventricular pacing mode may include delivery of other cardiac pacing therapies when needed as determined based on evaluations of the heart rhythm or other physiological sensors. Other therapies that may be delivered include, for example, cardiac resynchronization therapy, extra systolic stimulation, arrhythmia prevention therapies, and overdrive pacing.

At block 184, the device determines if ischemia is detected. The device may rely on any ischemia detection method available, including but not limited to ECG/EGM signal analysis, physiological sensor data, and patient feedback provided with the use of an external device such as the activator shown in FIG. 3 or other feedback method such as physical tapping on the device. During automatic ischemia detection, intermittent ventricular paced cycles that may occur during minimum ventricular pacing mode may be ignored, particularly when the ischemia detection is based on an analysis of ECG/EGM morphology. If ischemia is not detected, the device continues operating according to the normal programmed operating parameters and operating mode (block 182).

In response to detecting an ischemic episode, the frequency of ischemia monitoring using ECG/EGM signals and/or other physiological signals may be increased as indicated at block 186. During normal operation, ischemia monitoring may be programmed to occur at a periodic interval, for example every 4 hours. Ischemia monitoring may also occur on a triggered basis, for example in response to a high heart rate, change in blood pressure, change in activity level, or other detected physiological condition. If ischemia is detected, either by the implanted device or upon receipt of an external, manually generated signal, the frequency of ischemia monitoring may be increased, for example to every hour. In addition or alternatively to adjusting the ischemia monitoring frequency at block 186, the sampling rate used in acquiring the ECG/EGM signals and/or other physiological signals used in monitoring for ischemia may be adjusted to obtain a higher resolution signal(s). A higher signal resolution may allow more detailed signal analysis and more reliable detection of ischemia.

At block 188, an ischemia response is provided. As will be described in greater detail below, the ischemia response may include altering the current pacing mode by performing a mode switch or altering a pacing control parameter. Pacing control parameters that may be altered include, but are not limited to, timing intervals, rates, and pacing electrode configurations. The ischemia response may alternatively or additionally include altering arrhythmia detection methods and/or programmed arrhythmia therapies. The ischemia response may include alerting the patient using the patient alarm circuitry 166 shown in FIG. 2 to notify the patient of the ischemia episode. The patient can respond to an ischemia notification according to clinician instructions, for example by modifying their activity or by seeking medical attention.

At block 190, the device continues to monitor ischemia, at the adjusted monitoring frequency. If ischemia is still being detected, therapy alterations provided by the ischemia response may be maintained at block 194. Alternatively, the ischemia response provided at block 194 in response to a sustained or worsening state of ischemia, as detected at block 190, may include a different response than the initial ischemia response provided at block 188.

A response to a prolonged or worsening ischemic state provided at block 194 may include further alteration of the pacing mode and/or arrhythmia detection criteria and therapies and may include delivering a higher level physician or patient warning. Further alterations in the pacing mode may include switching to a non-rate responsive mode, adjusting the lower pacing rate, adjusting timing parameters, changing pacing electrode configuration, or attempting other available pacing modes or therapies. A pacing mode, control parameter settings, or other data relating to the ICD operating status at the time of the alleviation of the ischemia episode may be stored at block 196. Such data may be used by the ICD in providing the first response (block 188) to later ischemia episode detections.

When ischemia is no longer detected at block 190, the frequency of ischemia monitoring and/or signal sampling rate may be decreased at block 198. The reduction in ischemia monitoring frequency or sampling rate may occur after a delay following the end of the ischemic episode to ensure that an early recurrence of ischemia does not go undetected. After ischemia is no longer detected, the device returns to the normal programmed operating mode at block 182.

Figure 6:
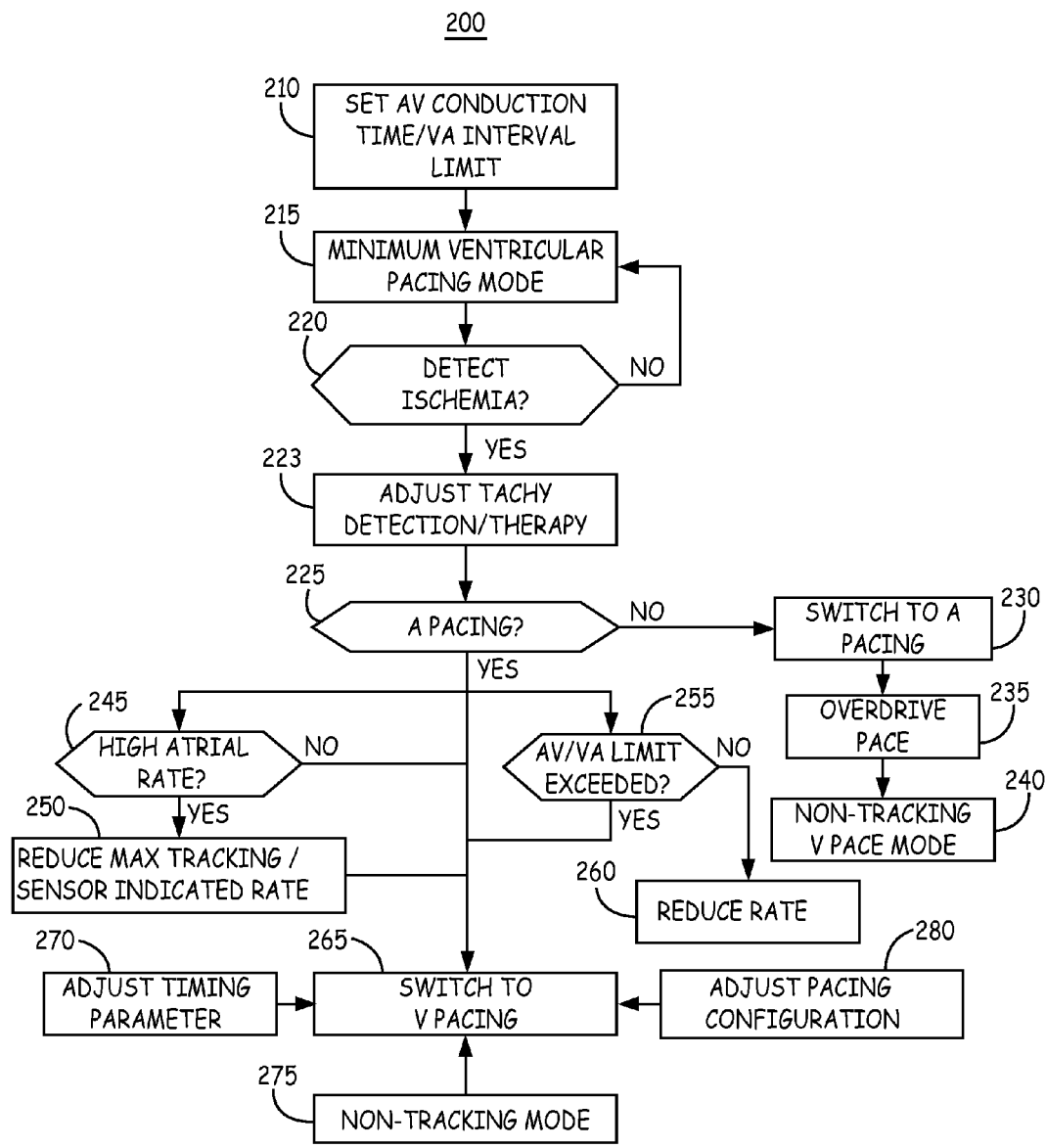
FIG. 6 is a flow chart summarizing a method for responding to myocardial ischemia detection according to one embodiment of the invention.

FIG. 6 is a flow chart summarizing a method for responding to myocardial ischemia detection according to one embodiment of the invention. Flow chart 200 is intended to illustrate a number of responses that may be provided by a device programmed to operate in a minimum ventricular pacing mode. While flow chart 200 is shown with a particular operational flow indicated by the arrows joining the various operational blocks, it is to be understood that numerous protocols that include one or more of the ischemia response operations shown and described herein may be developed for providing an appropriate response to myocardial ischemia. Accordingly, the particular order of the blocks shown in flow chart 200 may be rearranged, with additions or deletions, to achieve a desired response to myocardial ischemia in a device adapted for operating in a minimum ventricular pacing mode.

In general, the device monitors cardiac activity and delivers cardiac stimulation in the form of pacing or cardioversion/defibrillation shocks as needed in accordance with a programmed operating mode. During normal device operation, ischemia monitoring occurs, either on a periodic, triggered or continuous basis. In response to detecting an ischemic episode, device operation is modified. Numerous modifications, as will be described below, may be made, including modifications to pacing control parameters, pacing mode, arrhythmia detection parameters, and/or arrhythmia therapy delivery. Generally, modifications made in response to ischemia detection are made to alleviate the ischemia by reducing the demand placed on the heart and/or improve perfusion of the heart. Other modifications may be made to alter arrhythmia detection and therapies during an ischemic episode.

At block 210, an AV conduction time limit or a VA time interval limit may be programmed by a user or stored as nominal values in device memory. It is generally assumed that the device will operate in a minimum ventricular pacing mode of operation as indicated at block 215. A minimum ventricular pacing mode generally includes operating in an atrial pacing mode, for example AAI, ADI, AAIR, or ADIR, in order to allow intrinsic conduction from the atria to the ventricles to occur and subsequent intrinsic ventricular depolarization. The atrial pacing mode is maintained as long as atrial-ventricular conduction remains intact. During the atrial pacing mode, if a ventricular sense event does not occur between two consecutive atrial events, i.e. if AV conduction becomes blocked, the device will switch to a pacing mode that includes ventricular pacing, typically a dual chamber mode such as DDD, DDI, DDDR, or DDIR. Apparatus and methods for delivering pacing to ensure AV conduction whenever possible are generally described in U.S. Pat. No. 6,772,005 (Casavant, et al.) and U.S. Pat. Pub. No. 2005/0267539 (Betzold et al.), both of which are hereby incorporated herein by reference in their entirety.

During an atrial pacing mode, AV conduction may remain intact but AV conduction time may become relatively long. At long AV conduction times, the ventricle contracts late in the cardiac cycle. A subsequent atrial contraction may occur prior to the end of passive ventricular filling. The force available from the contracting atria is under utilized when blood is forced into an empty or only partially filled ventricle. Overall filling is reduced. The atrial force, often referred to as the atrial "kick", is better utilized after passive filling is complete to force additional blood into the ventricle, which promotes a strong ventricular contraction on the next cardiac cycle according to Starling's Law.

On the other hand, if the AV conduction time is short, the ventricles may contract early in the cardiac cycle, before filling is complete. The atrial may contract against a closed or partially closed valve causing a reversal in blood flow. Improper atrial-ventricular coupling can decrease cardiac output and myocardial perfusion, causing or exacerbating an ischemic state. During an atrial pacing mode that is intended to allow intrinsic AV conduction to occur whenever possible, improper AV coupling may lead to or worsen myocardial ischemia. As such, limits to the AV conduction time may be set to ensure that ventricular depolarization occurs after atrial depolarization at an acceptable coupling interval. Additionally or alternatively, VA time interval limits may be set to ensure that the relative timing of an intrinsic ventricular depolarization and the subsequent atrial pace or sense event is consistent with an acceptable coupling interval. Maximum and/or minimum AV conduction time and/or VA time interval limits may be set at block 210. As will be described below, if ischemia is detected during an atrial pacing mode, an ischemia response may include measuring the AV conduction time and/or VA time interval. If the AV conduction time measurement or a VA time interval measurement crosses a predefined limit, the ischemia response may further include a modification of the pacing mode and/or pacing control parameters. For example, the pacing mode may be altered to include LV pacing at a short AV interval to improve AV coupling, particularly when a long AV or short VA interval is observed during atrial-only pacing.

At step 215, the device operates in a minimum ventricular pacing mode. The minimum ventricular pacing mode includes at least one atrial pacing mode intended to allow intrinsic AV conduction to occur whenever possible and at least one pacing mode that includes ventricular pacing to ensure ventricular depolarization when AV block occurs. Accordingly, the pacing mode may switch between an atrial-only pacing mode and a ventricular pacing mode (which includes dual chamber modes) as needed during the minimum ventricular pacing mode of operation. However, it is recognized that the device may, at times, deliver other pacing therapies when needed such as anti-tachycardia pacing therapies, cardiac resynchronization therapy, extra systolic stimulation therapy, arrhythmia prevention therapies, or other pacing therapies.

At block 220, the device determines if ischemia is detected. If ischemia is detected, an ischemia response may include adjusting arrhythmia detection parameters and/or programmed arrhythmia therapies as indicated by block 223. A clinician may program ischemia response arrhythmia detection requirements and/or therapies to be different than those applied during periods of non-ischemic. A clinician may select more aggressive or less aggressive tachycardia detection and therapies depending on patient history and additional physiological sensor data. For example, more aggressive arrhythmia detection requirements, such as a lower NID, may be relied upon during a detected ischemic episode since the ischemic myocardium may be more vulnerable to arrhythmias. In another example, a programmed therapy may be cancelled or delayed since the ischemia may be the cause of the arrhythmia. The ischemic myocardium may not respond well to a particular programmed therapy.

Following an ischemia detection at block 220, an ischemic response may include determining the current pacing mode as indicated at block 225. The pacing mode may be altered in an attempt to alleviate the ischemia. If the device is not currently operating in an atrial-only pacing mode, as determined at block 225, the device may switch to an atrial-only pacing mode as indicated at block 230. Myocardial ischemia may be more prevalent when ventricular pacing is delivered. As such, the ventricular pacing may be minimized or reduced by switching to an atrial-only pacing mode while continuing to monitor for AV conduction such that ventricular pacing may be restored if needed to ensure ventricular depolarization.

In some embodiments, atrial overdrive pacing may be delivered in response to ischemia detection, as indicated at block 235. AV conduction block may be induced by overdrive pacing in the atrium. The pacing mode may then be switched to a non-tracking ventricular pacing mode at block 240 to control the ventricular rate so as to reduce demand in an attempt to alleviate the ischemia. The response of converting to an overdrive atrial pacing rate may be performed independent of the initial pacing mode, determined at block 225, at the time of ischemia detection. In a single chamber device, operating in an AAI or AAIR mode, ventricular sensing would be performed to ensure ventricular asystole does not occur during atrial overdrive pacing. The atrial overdrive pacing would be suspended in the presence of complete AV block.

If the current pacing mode at the time of ischemia detection is an atrial pacing mode, as determined at block 225, the ischemia response may include switching to a pacing mode that includes ventricular pacing at block 265. A "ventricular pacing mode" as referred to herein refers to pacing modes that include ventricular pacing and may or may not include atrial pacing. Furthermore, ventricular pacing modes may include pacing therapies such as cardiac resynchronization therapy or extra systolic stimulation which include the delivery of ventricular pacing pulses. Ventricular pacing modes, in particular dual or multi-chamber modes, may act to alleviate ischemia by improving AV coupling or improving cardiac output. Ventricular pacing modes that include LV or bi-ventricular pacing may be more beneficial than ventricular pacing modes that are limited to RV pacing.

In another embodiment, the ischemia response may include measuring an AV conduction time and/or VA time interval during atrial pacing. AV conduction time and VA time intervals may be measured according to methods known in the art, for example by measuring the time interval between an atrial sensed or paced event and a sensed R-wave. If an AV conduction time or VA time interval limit is crossed, as determined at block 255, the device converts to a pacing mode that includes ventricular pacing at block 265. If the AV conduction time and VA time interval do not cross pre-set limits (block 210), atrial pacing may be maintained without an alteration to the pacing mode. Alternatively, an atrial pacing rate may be reduced at block 260 to reduce myocardial demand in an attempt to alleviate ischemia. It is recognized that a reduction in pacing rate at block 260 may be made directly in response to an ischemia detection, regardless of the initial pacing mode or other criteria such as an AV conduction time limit.

In another embodiment, an ischemia response includes determining if the atrial rate is high, e.g. during sinus tachycardia, as indicated at block 245. If the atrial rate is high and an ischemia detection is made, pacing control parameters may be altered by reducing a maximum tracking rate and/or reducing a maximum rate responsive sensor-indicated rate as indicated at block 250. Reduction of a maximum ventricular rate may be followed by switching to a ventricular pacing mode at block 265 if the initial pacing mode was an atrial-only pacing mode (block 225) and a high atrial rate was detected (block 245). It is recognized that if the initial pacing mode included ventricular pacing at the time of ischemia detection, the adjustment of a maximum tracking rate and/or maximum sensor-indicated rate in response to the ischemia detection may be made without a pacing mode switch.

If the initial pacing mode includes ventricular pacing, or if the ischemia response includes a mode switch to a ventricular pacing mode at block 265 the ischemia response may include altering the ventricular pacing mode. For example, the ischemia response may include altering a timing control parameter, such as an AV delay or a VV delay, as indicated at block 270. Adjusting a timing interval may include searching for an optimal time interval which results in an alleviation of the ischemia.

In other embodiments the ischemia response may include switching to a non-tracking mode as indicated at block 275. Additionally or alternatively, the ischemia response may include changing a ventricular pacing configuration, for example by switching from left ventricular pacing to bi-ventricular pacing or vice versa, as indicated at block 280. Changing a timing parameter at block 270 and/or changing the pacing configuration at block 280 may have a beneficial effect on AV coupling or the synchronization between the right and left ventricles, thereby improving cardiac output and myocardial perfusion. Converting to a non-tracking mode at block 275 will act to reduce demand by maintaining the ventricular rate at a lower rate.

Thus, apparatus and associated methods have been presented in the foregoing description with reference to specific embodiments for providing a response to the detection of myocardial ischemia. It is appreciated that various modifications to the referenced embodiments may be made without departing from the scope of the invention as set forth in the following claims.

We claim:

1. A method for delivering cardiac pacing with an implantable medical device to a patient having a heart having an atrium and a ventricle, comprising the steps of:
   delivering the cardiac pacing;
   detecting myocardial ischemia; then if the myocardial ischemia is detected and the cardiac pacing is in an atrial-only pacing mode at a first time, altering the cardiac pacing to an atrial and ventricular pacing mode; and
   if the myocardial ischemia is detected and the cardiac pacing is in the atrial and ventricular pacing mode at a second time, different from the first time, altering the cardiac pacing to the atrial-only pacing mode.

2. The method of claim 1 further comprising the step, before each of the altering the cardiac pacing steps, of measuring a time interval between an atrial event and an intrinsic ventricular event, and wherein the cardiac pacing is altered from the atrial-only pacing mode to the atrial and ventricular pacing mode if the myocardial ischemia is detected, the cardiac pacing is in the atrial-only pacing mode and the time interval exceeds a predetermined limit.

3. The method of claim 1 wherein altering the cardiac pacing to an atrial and ventricular pacing mode includes altering a ventricular pacing configuration.

4. The method of claim 1 wherein altering the cardiac pacing to an atrial and ventricular pacing mode includes adjusting an atrial-ventricular delay.

5. The method of claim 1 wherein altering the cardiac pacing to an atrial and ventricular pacing mode includes adjusting a maximum tracking rate if the atrial-only pacing mode is a high-rate atrial pacing mode.

6. The method of claim 1 wherein altering the cardiac pacing to an atrial and ventricular pacing mode includes adjusting a maximum sensor indicated rate if the atrial-only pacing mode is a high-rate atrial pacing mode.

7. The method of claim 1 wherein altering the cardiac pacing to the atrial-only pacing mode includes delivering overdrive pacing in the atrium, and, if a loss of atrial-ventricular (AV) conduction is subsequently detected, switching from the atrial-only pacing mode to a non-tracking ventricular pacing mode.

8. The method of claim 1, further comprising the step, after the detecting myocardial ischemia step and before the altering the cardiac pacing steps, of adjusting a programmed arrhythmia detection criterion in response to detecting the myocardial ischemia.

9. The method of claim 1, further comprising the step, after the detecting myocardial ischemia step and before the altering the cardiac pacing steps, of adjusting a programmed tachycardia therapy in response to detecting the myocardial ischemia.

10. An implantable medical device system adapted to deliver cardiac pacing, comprising:
   a plurality of electrodes;
   an output circuit coupled to the plurality of electrodes for delivering cardiac pacing;
   means for detecting myocardial ischemia;
   a control circuit, operatively coupled to the output circuit, for controlling the delivery of cardiac pacing pulses by the output circuit; and
   a processor, coupled to the control circuit and the means for detecting myocardial ischemia, configured to:
      alter the cardiac pacing to an atrial and ventricular pacing mode if the cardiac pacing is an atrial-only pacing mode and if the detecting means detect myocardial ischemia; and
      alter the cardiac pacing to an atrial-only pacing mode if the cardiac pacing is in an atrial and ventricular mode and if the detecting means detect myocardial ischemia.

11. The system of claim 10 wherein the processor is further configured to measure a time interval between an atrial event and an intrinsic ventricular event and wherein the processor alters the cardiac pacing from the atrial-only pacing mode to the atrial and ventricular pacing mode if the myocardial ischemia is detected, the cardiac pacing is in the atrial-only pacing mode and the time interval exceeds a predetermined limit.

12. The system of claim 10 further comprising switching circuitry, operatively coupled to the processor, for selecting individual ones of the plurality of electrodes; and
   wherein the processor alters the cardiac pacing by adjusting a pacing electrode configuration of the plurality of electrodes using the switching circuitry.

13. The system of claim 10 wherein the processor is configured to adjust an atrial-ventricular delay.

14. The system of claim 10 wherein the processor is configured to adjust a maximum tracking rate if the atrial-only pacing mode is a high-rate atrial pacing mode.

15. The system of claim 10 wherein the processor, when altering the cardiac pacing to an atrial-only pacing mode is further configured to deliver overdrive pacing in an atrial chamber, and wherein, if the processor detects a loss of atrial-ventricular (AV) conduction the processor is configured to switch from the atrial-only pacing mode to a non-tracking ventricular pacing mode.

16. The system of claim 10 wherein the processor is configured to adjust a programmed tachycardia detection criterion in response to detecting the myocardial ischemia by the means for detecting myocardial ischemia.

17. The system of claim 10 wherein the processor is configured to adjust a programmed tachycardia therapy in response to detecting the myocardial ischemia by the means for detecting myocardial ischemia.

18. A non-transitory computer readable medium for storing a set of instructions which when implemented in an implantable medical device system cause the system to perform a method for delivering cardiac pacing with an implantable medical device to a patient having a heart having an atrium and a ventricle, comprising the steps of:
   delivering the cardiac pacing;
   detecting myocardial ischemia; then
   if the myocardial ischemia is detected and the cardiac pacing is in an atrial-only pacing mode at a first time, altering the cardiac pacing to an atrial and ventricular pacing mode; and
   if the myocardial ischemia is detected and the cardiac pacing is in the atrial and ventricular mode at a second time, different than the first time, altering the cardiac pacing to the atrial-only pacing mode.

19. A method for delivering a cardiac therapy with an implantable medical device to a patient with a heart having an atrium and a ventricle, comprising the steps of:
   delivering the cardiac therapy only to the atrium of the patient; then
   measuring the time interval between sequential depolarizations of the atrium and the ventricle; then
   if the time interval between sequential depolarizations of the atrium and the ventricle is outside of a predetermined range, delivering the cardiac therapy to both the atrium and the ventricle; then
   detecting a myocardial ischemia in the patient; then
   if the cardiac therapy is being delivered only to the atrium of the patient and the myocardial ischemia is detected, delivering the cardiac therapy to both the atrium and the ventricle; else
   if the cardiac therapy is being delivered to both the atrium and the ventricle and the myocardial ischemia is detected, delivering the cardiac therapy to only the atrium.

20. The method of claim 19, wherein the delivering the cardiac therapy to both the atrium and the ventricle after the detecting a myocardial ischemia step occurs if the cardiac therapy is being delivered only to the atrium of the patient and the myocardial ischemia is detected and if the time interval between sequential depolarizations of the atrium and the ventricle is outside of the range.

21. The method of claim 20 wherein the cardiac therapy is delivered at a pacing rate; and
   further comprising the step, after the detecting a myocardial ischemia step, of reducing the pacing rate if the cardiac therapy is being delivered only to the atrium of the patient and the myocardial ischemia is detected and if the time interval between sequential depolarizations of the atrium and the ventricle is within the range.

22. The method of claim 19 wherein the cardiac therapy has a maximum tracking rate; and
   further comprising the step, after the detecting a myocardial ischemia step, of detecting a depolarization rate of the atrium of the patient; and then
   reducing the maximum tracking rate of the cardiac therapy if the cardiac therapy is being delivered only to the atrium of the patient and the myocardial ischemia is detected and the depolarization rate of the atrium of the patient exceeds a threshold.

23. The method of claim 19 wherein the cardiac therapy has a maximum sensor indicated rate; and
   further comprising the step, after the detecting a myocardial ischemia step, of detecting a depolarization rate of the atrium of the patient; and then
   reducing the maximum sensor indicated rate of the cardiac therapy if the cardiac therapy is being delivered only to the atrium of the patient and the myocardial ischemia is detected and the depolarization rate of the atrium of the patient exceeds a threshold.

24. The method of claim 19, wherein the delivering the cardiac therapy to only the atrium of the patient step after the detecting a myocardial ischemia step further comprises:
   delivering the cardiac therapy as an overdrive pacing therapy to the atrium of the patient; then
   detecting a loss of conduction between the atrium and the ventricle; then
   delivering the cardiac therapy to the ventricle in a non-tracking mode.

25. The method of claim 19, further comprising the step, after the detecting myocardial ischemia step, of adjusting a programmed arrhythmia detection criterion in response to detecting the myocardial ischemia.

26. The method of claim 19, further comprising the step, after the detecting myocardial ischemia step, of adjusting a programmed tachycardia therapy in response to detecting the myocardial ischemia.

27. A method for delivering cardiac pacing with an implantable medical device to a patient having a heart having an atrium and a ventricle, comprising the steps of:
 delivering the cardiac pacing;
 detecting myocardial ischemia; then
 if the myocardial ischemia is detected and the cardiac pacing is in an atrial-only pacing mode altering the cardiac pacing to an atrial and ventricular pacing mode.

28. The method of claim 27 further comprising the step, before the altering the cardiac pacing step, of measuring a time interval between an atrial event and an intrinsic ventricular event, and wherein the cardiac pacing is altered from the atrial-only pacing mode to the atrial and ventricular pacing mode if the myocardial ischemia is detected, the cardiac pacing is in the atrial-only pacing mode and the time interval exceeds a predetermined limit.

29. The method of claim 27 wherein altering the cardiac pacing to an atrial and ventricular pacing mode includes altering a ventricular pacing configuration.

30. The method of claim 27 wherein altering the cardiac pacing to an atrial and ventricular pacing mode includes adjusting an atrial-ventricular delay.

31. The method of claim 27 wherein altering the cardiac pacing to an atrial and ventricular pacing mode includes adjusting a maximum tracking rate if the atrial-only pacing mode is a high-rate atrial pacing mode.

32. The method of claim 27 wherein altering the cardiac pacing to an atrial and ventricular pacing mode includes adjusting a maximum sensor indicated rate if the atrial-only pacing mode is a high-rate atrial pacing mode.

\* \* \* \* \*